United States Patent

De Maldé et al.

Patent Number: 5,354,507
Date of Patent: Oct. 11, 1994

[54] INHIBITION OF STEEL CORROSION

[75] Inventors: Viviana De Maldé; Luigi Rivola; Arnaldo Roggero; Alberto Gandini, all of Milan, Italy

[73] Assignee: Eniricerche S.p.A, Milan, Italy

[21] Appl. No.: 7,116

[22] Filed: Jan. 21, 1993

[30] Foreign Application Priority Data

Jan. 22, 1992 [IT] Italy ................ MI92 A 000107

[51] Int. Cl.$^5$ ............................. C23F 11/14
[52] U.S. Cl. ................... 252/390; 252/394; 422/16; 540/470; 564/279
[58] Field of Search ................ 422/16; 252/394, 390, 252/392; 540/470; 564/279

[56] References Cited

U.S. PATENT DOCUMENTS

| | | | |
|---|---|---|---|
| 4,065,496 | 12/1977 | Oppolzer | 564/204 |
| 4,980,074 | 12/1990 | Henson et al. | 252/8.555 |
| 4,986,962 | 1/1991 | Cesari et al. | 422/16 |

FOREIGN PATENT DOCUMENTS

| | | |
|---|---|---|
| 156631 | 10/1985 | European Pat. Off. |
| 188353 | 7/1986 | European Pat. Off. |
| 405719 | 1/1990 | European Pat. Off. |

Primary Examiner—Robert L. Stoll
Assistant Examiner—Valerie D. Fee
Attorney, Agent, or Firm—Rogers & Wells

[57] ABSTRACT

Compounds of general formula $$CH_3-[CH-CH_2]_m-(CH=CH)_n-CH=N-R \quad (I)$$
$$\underset{NHR}{|}$$

wherein:

R is a linear or branched $C_1$–$C_{20}$ alkyl radical, m is either 0 or 1; n has a value of from 1 to 10, are corrosion inhibitors, suitable for inhibiting the general corrosion and the stress brittlening caused by hydrogen sulfide (SSC), in an acidic environment, in the presence, or absence of carbon dioxide, of medium-and high-strength manganese steels and low-alloy steels, commonly used in petrochemical facilities and in bore drilling, transport and processing systems for natural gas or petroleum.

15 Claims, No Drawings

INHIBITION OF STEEL CORROSION

The present invention relates to steel corrosion inhibitors, and to their use in inhibiting the corrosion of medium- and high-strength manganese steels and low-alloy steels.

Corrosion, as a process of decay of metal materials used in the construction of structures and production facilities, causes enormous direct and indirect damages. In particular, the corrosion of medium- and high-strength manganese steels and low-alloy steels, which are the steel grades which are commonly used in he petrochemical industry, besides the gas and petroleum production, extraction and transport systems, represents a serious problem because the normal corrosive action of water and oxygen is enhanced and made faster by the presence of carbon dioxide, besides organic and inorganic salts and acids.

Particularly serious is stress corrosion in the presence of hydrogen sulfide (SSC), frequently observed in crude oil extraction facilities. The resulting brittlening, together with the general corrosion, of these steels submitted to considerably high mechanical stresses, leads often to the development of cracking and microfractures in the material and causes serious yielding and mechanical collapse risks.

U.S. Pat. No. 4,986,962 discloses compounds having mono- or di-azomethinic structure, which are capable of inhibiting stress corrosion in the presence of hydrogen sulfide in Low- and medium-strength manganese steels and low-alloy steels.

The present Applicant found now, according to the present invention, that particular compounds of essentially aliphatic nature, bearing an ethylenic unsaturation -CH=CH- in the alpha-position to the -CH-N- group, constitute corrosion inhibitors which, as compared to those known from the prior art, display an unexpectedly good protective action against general corrosion, and brittlening in the presence of hydrogen sulfide (SSC), of high- and medium-strength manganese steels and low-alloy steels.

In accordance therewith, the present invention relates to compounds having the formula:

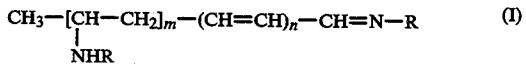

(I)

wherein:

R is a linear or branched $C_1$-$C_{20}$ alkyl radical, m is either 0 or 1; n has a value of from 1 to 10, with reference to their use as steel corrosion inhibitors.

According to the preferred embodiment, R is a straight or branched $C_8$-$C_{18}$ alkyl radical, m is 0 and n has a value of from 2 to 6.

The inhibitors according to the present invention can additionally contain minor amounts ($\leq 15$ mol %) of dimer compounds which can generally be represented with the formula:

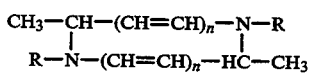

wherein R and n have the same meaning has reported for formula (I). Also the dimer compounds are per se endowed with corrosion-inhibiting characteristics, Thus, according to a particular embodiment, the inhibitors according to the present invention are constituted by a mixture of the following compounds:

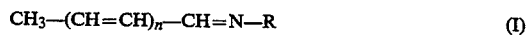

(I)

wherein R is a straight or branched $C_1$-$C_{20}$ alkyl, and preferably a $C_8$-$C_{18}$ alkyl radical, n has a value comprised within the range of from 1 to 10 and preferably of from 2 to 6;

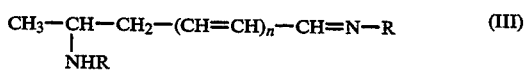

(III)

wherein R and n have the same meaning as reported for formula (I), and possible isomeric forms of compound (III); and

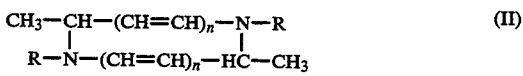

(II)

wherein R and n have the same meaning as reported for formula (I), with the component (I) being present in the mixture in an amount comprised within the range of from 50 to 95 mol %, the component (III) being present in an amount comprised within the range of from 0 to 40 mol %, and the component (II) being present in an amount of from 0 to 15 mol % with the proviso that the components (III) and/or (II) account for at least 5 mol % of the same mixture.

The corrosion inhibitor compounds according to the present invention can be obtained by causing an aliphatic amine R-$NH_2$, wherein R have the above reported meaning, to react with a suitable unsaturated aldehyde, as, e.g., crotonic aldehyde or sorbic aldehyde. Examples of suitable amines are octylamine, decylamine undecylamine, dodecylamine, hexadecylamine or mixtures of $C_8$-$C_{18}$ amines.

The reaction is generally carried out by bringing the aldehyde and the amine into contact with each other in a mutual molar ratio of from 10:1 to 1:1, operating at a temperature comprised within the range of from 20° to 160° C. and for a time of from 1 to 18 hours, preferably in the presence of an inert organic solvent, such as, e.g., toluene. It should be observed that when the reaction is carried out with a reactant ratio in the high region of the range, some unreacted aldehyde remains in the reaction mixture and said aldehyde must be removed, for example by distillation. When, on the contrary, the reaction is carried out within the low region of said reactant ratios in the reaction mixture some unreacted amine remains, which needs not be separated from the same mixture.

Therefore, according to the preferred embodiment, the process is carried out with a molar ratio of aldehyde to amine of the order of 1.5:1–1:1, because this makes it possible the reaction products to be directly used without any preliminary separation of unaltered amine.

It was furthermore found, according to the present inventions that the corrosion inhibitor compounds can be obtained by causing an aliphatic amine R-$NH_2$, wherein R has the same meaning as reported hereinabove, to react with acetaldehyde, by operating under suitable conditions for favouring a secondary reaction of condensation of the same acetaldehyde, so as to produce the corrosion inhibitor compounds in one single reaction step. The conditions favouring the secondary reaction of condensation of acetaldehyde are the excess of acetaldehyde [depending on the desired value of n in formula (I)—typically a molar ratio of acetaldehyde to amine of the order of 1.5:1]; the slow addition of acetaldehyde to the amine; and the continuous removal of water from the reaction mixture.

By operating under these conditions, reaction products are obtained, the NMR spectra of which display the formation of compounds of Schiff base type, in which the initial aldehydic chain is replaced by an unsaturated aliphatic chain with conjugated unsaturations, deriving from the condensation of the aldehyde used as the starting material.

According to a particular embodiment, the present invention relates to a method for the inhibiting general corrosion and stress brittlening in the presence of hydrogen sulfide (SSC), in an acidic environment, in the presence, or absence, of carbon dioxide, of medium- and high-strength manganese steels and low-alloy steels, used in petrochemical facilities and in natural gas or petroleum drilling, transport and processing systems, which comprises dissolving one or more inhibitor compound(s) above described, in an aqueous or water-alcoholic solvent, and injecting the resulting solution into the facility or system which has to be protected from corrosion.

Generally, the concentration of said inhibitors in the relevant solvent will be comprised within the range of from 1 to 500 ppm (parts per million parts by weight) and preferably of from 2 to 200 ppm, and, in the most preferred embodiment, of from 15 to 100 ppm.

Specific examples of medium- and high-strength manganese steels and low-alloy steels which can be protected according to the present invention are those known as API 5L X60, API 5L X65, API 5L X70, P-110 and the like.

In particular, by operating according to the present invention optimal results are achieved in the protection of the above mentioned steels from the effects of corrosion and stress corrosion.

As it may be observed from the following experimental examples, the inhibitors according to the present invention display an unexpectedly improved effect against general corrosion. In particular, the values of corrosion current, as determined through the polarization curve, are approximately five times lower than as obtainable with the azomethines known from the prior art.

EXAMPLE 1

A solution of dodecylamine (0.10 equivalents) in toluene (150 ml) is charged to a three-neck flask of 500 ml of capacity, equipped with thermometer, stirrer, dropping funnel and distillation unit with phase-separation burette (Marcusson head). Into such a solution, kept stirred and heated at solvent boiling temperature, acetaldehyde (0.15 equivalents) dissolved in 50 ml of toluene is dropwise added, with a very slow addition rate. The reaction is favoured by the removal, through the water-toluene azeotropic mixture, of water formed during the process of amine-aldehyde condensation: the water separated from the azeotropic mixture is discharged and the solvent is recycled to the reaction flask.

The synthesis is carried out for approximately 2 hours, until pure solvent starts to distil. The solvent is distilled off and a mixture is obtained, which is constituted by the following compounds:

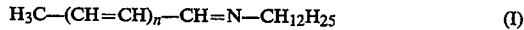
$$H_3C-(CH=CH)_n-CH=N-CH_{12}H_{25} \quad (I)$$

wherein n has an average value of about 3, in an amount of 55 mol %,

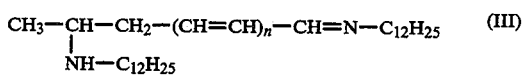
$$CH_3-\underset{\underset{NH-C_{12}H_{25}}{|}}{CH}-CH_2-(CH=CH)_n-CH=N-C_{12}H_{25} \quad (III)$$

wherein n has an average value of about 3, in an amount of 33 mol %, and

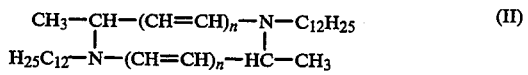
$$CH_3-\underset{\underset{H_{25}C_{12}-N-(CH=CH)_n-HC-CH_3}{|}}{CH}-(CH=CH)_n-N-C_{12}H_{25} \quad (II)$$

wherein n has an average value of about 2, in an amount of 11 mol %.

These structures were determined by means of physical-chemical analyses, in particular NMR and GC-MS (gaschromatography-mass) analyses.

An at all similar mixture is obtained by operating as disclosed hereinanbove and using, as the reaction solvent, tetrahydrofuran, in lieu of toluene.

EXAMPLE 2

The process is carried similarily to Example 1, with the difference that instead of acetaldehyde, crotonic aldehyde is used, and a mixture is obtained of the following compounds:

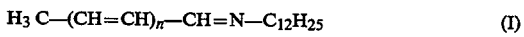
$$H_3C-(CH=CH)_n-CH=N-C_{12}H_{25} \quad (I)$$

wherein n has an average value of about 4, in an amount of 85 mol %,

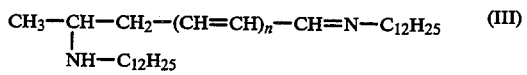
$$CH_3-\underset{\underset{NH-C_{12}H_{25}}{|}}{CH}-CH_2-(CH=CH)_n-CH=N-C_{12}H_{25} \quad (III)$$

wherein n has an average value of about 4, in an amount of 10 mol %, and

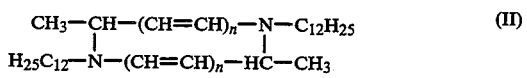
$$CH_3-\underset{\underset{H_{25}C_{12}-N-(CH=CH)_n-HC-CH_3}{|}}{CH}-(CH=CH)_n-N-C_{12}H_{25} \quad (II)$$

wherein n has an average value of about 2, in an amount of 5 mol %.

EXAMPLE 3

The process is carried similarily to Example 1, with the difference that instead of acetaldehyde, sorbic aldehyde is used, and a mixture is obtained of the following compounds:

$$H_3C-(CH=CH)_n-CH=N-C_{12}H_{25} \quad (I)$$

wherein n has an average value of about 2, in an amount of 88 mol %,

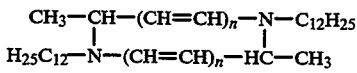

$$\begin{array}{c} CH_3-CH-(CH=CH)_n-N-C_{12}H_{25} \\ | \quad\quad\quad\quad\quad\quad\quad | \\ H_{25}C_{12}-N-(CH=CH)_n-HC-CH_3 \end{array} \quad (II)$$

wherein n has an average value of about 2, in an amount of 11 mol %.

EXAMPLE 4

In order to evaluate the corrosion inhibiting effect, the hydrogen permeation ($I_{perm}$) and corrosion ($I_{corr}$) currents are measured in steel specimens in the absence of inhibitors, and in the presence of inhibitors.

In greater detail, specimens of API 5L ×70 steel are immersed in a standard aqueous solution at pH 2.6 (NACE method TM 01-77) containing acetic acid (0.5% by weight) and sodium chloride (5% by weight), saturated with hydrogen sulfide, in the absence of inhibitor, or in the presence of 25 ppm of inhibitors.

For the measurements of hydrogen permeation current, laminar metal specimens of 2 mm of thickness are used, and for the measurements of corrosion current, cylindrical specimens with a total surface-area of approximately 4.5 cm$^2$, are used.

The results are reported in following Table I, in which I.E.% indicates the percent inhibitor power.

TABLE I

| Inhibitor, Example No. | $I_{perm}$ ($\mu$A/cm$^2$) | I.E. % (%) | $I_{corr}$ ($\mu$A/cm$^2$) | I.E. % (%) |
|---|---|---|---|---|
| 1 | 0.20 | 96.9 | 1.1 | 99.7 |
| 2 | 0.19 | 97.0 | 5.9 | 98.4 |
| 3 | 0.23 | 96.5 | 1.2 | 99.6 |
| none | 6.53 | — | 372.3 | — |

EXAMPLE 5

The test is carried out as in Example 4, using X-65 steel as laminar specimens of 2 mm of thickness. The results are reported in following Table II.

TABLE II

| Inhibitor, Example No. | $I_{perm}$ ($\mu$A/cm$^2$) | I.E. % (%) | $I_{corr}$ ($\mu$A/cm$^2$) | I.E. % (%) |
|---|---|---|---|---|
| 1 | 0.3 | 95.5 | 0.85 | 99.6 |
| 2 | 0.7 | 89.5 | 0.78 | 99.7 |
| none | 6.7 | — | 245.2 | — |

We claim:

1. A corrosion inhibiting composition comprising an aqueous or aqueous-alcoholic solvent and at least one corrosion inhibiting compound having the formula:

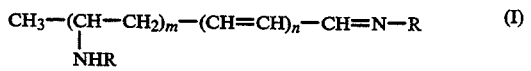

$$\begin{array}{c} CH_3-(CH-CH_2)_m-(CH=CH)_n-CH=N-R \\ | \\ NHR \end{array} \quad (I)$$

a dimer thereof having the formula:
where R is a linear or branched C$_1$-C$_{20}$ alkyl radical, m is either 0 or 1, and n is from 1 to 10, the corrosion inhibiting compound being useful to protect high- and medium-strength manganese steels and low-alloy steels against corrosion and brittlening in the presence of hydrogen sulfide and being present in a corrosion inhibiting amount of 1–500 ppm.

2. A composition according to claim 1, wherein in formula (I) R is a linear or branched C$_8$-C$_{18}$ alkyl radical, m is O, and n is from 2 to 6.

3. A composition according to claim 1, further comprising a dimer of compound (I), which dimer has the formula

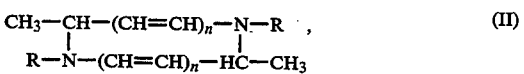

$$\begin{array}{c} CH_3-CH-(CH=CH)_n-N-R \\ | \quad\quad\quad\quad\quad\quad | \\ R-N-(CH=CH)_n-HC-CH_3 \end{array} \quad (II)$$

where R is a linear or branched C$_1$-C$_{20}$ alkyl radical and n is from 1 to 10 and which dimer is present in an amount up to 15 mol %.

4. A composition according to claim 3 further comprising

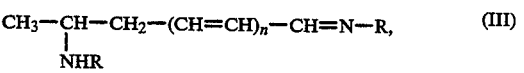

$$\begin{array}{c} CH_3-CH-CH_2-(CH=CH)_n-CH=N-R, \\ | \\ NHR \end{array} \quad (III)$$

where R is a linear or branched C$_1$-C$_{20}$ alkyl and n is 1 to 10.

5. A composition according to claim 3, wherein compound (I) is present in an amount of from 50 to 95 mol %, compound (IIA) is present in an amount of up to 40 mol %, and compound (II) is present in an amount of up to 15 mol %.

6. A composition according to claim 4, where R in each compound is a linear or branched C$_8$-C$_{18}$ alkyl radical and n is 2–6.

7. A composition according to claim 3, wherein in formula (I) R is a linear or branched C$_8$-C$_{18}$ alkyl radical, m is 0, and n is from 2 to 6.

8. A corrosion inhibiting composition comprising an aqueous or aqueous-alcoholic solvent and a mixture of corrosion inhibiting compounds having the formulas:

$$CH_3-(CH=CH)_n-CH=N-R \quad (I)$$

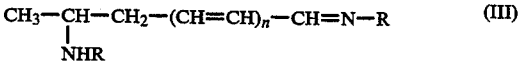

$$\begin{array}{c} CH_3-CH-CH_2-(CH=CH)_n-CH=N-R \\ | \\ NHR \end{array} \quad (III)$$

and

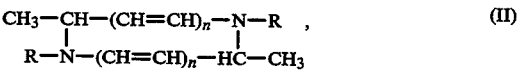

$$\begin{array}{c} CH_3-CH-(CH=CH)_n-N-R \\ | \quad\quad\quad\quad\quad\quad | \\ R-N-(CH=CH)_n-HC-CH_3 \end{array} \quad (II)$$

where R at each occurrence is a linear or branched C$_1$-C$_{20}$ alkyl radical, m is either 0 or 1, and n is 1–10; wherein compound (I) is present in an amount of from 50 to 95 mol %, compound (III) is present in an amount of up to 40 mol % and compound (II) is present in an amount of up to 15 mol %, with the proviso that compounds (III) and/or (II) account for at least 5 mol %; the corrosion inhibiting compounds being useful to protect high- and medium-strength manganese steels and low-alloy steels against corrosion and brittlening in the presence of hydrogen sulfide and being present in a corrosion inhibiting amount of 1–500 ppm.

9. A composition according to claim 8, where R is a linear or branched C$_8$-C$_{18}$ alkyl and n is 2–6.

10. A composition according to claim 8, wherein compound (I) is present in an amount of about 55 mol %; wherein compound (III) is present in an amount of about 33 mol %; wherein compound (II) is present in an amount of about 11 mol %; and wherein in compounds (I), (III) and (II) R is C$_{12}$-H$_{25}$ and n in compounds (I) and (III) has an average value of 3 and n in compound (II) has an average value of 2.

11. A composition according to claim 8, wherein compound (I) is present in an amount of 85 mol %; wherein compound (III) is present in an amount of 10 mol %; wherein compound (II) is present in an amount of 5 mol %; wherein in compounds (I), (III), and (II) R is $C_{12}-H_{25}$ and wherein in compounds (I) and (III) n has an average value of 3 and in compound (II) n has an average value of 2.

12. A composition according to claim 8, wherein compound (I) is present in an amount of about 88 mol %; wherein compound (II) is present in an amount of about 11 mol %; wherein in compounds (I) and (II) R is $C_{12}-H_{25}$; and wherein in compound (I) n has an average value of 3 and in compound (II) n has an average value of 2.

13. A method for inhibiting general corrosion and stress brittlening, in the presence of hydrogen sulfide, and in the presence or absence of carbon dioxide, of medium-strength and high-strength manganese steels and low-alloy steels used in a petrochemical facility and in natural gas or petroleum-drilling operations, transport and processing systems, which comprises injecting the corrosion inhibiting composition of claim 1 into the facility or the systems which are to be protected from corrosion.

14. A method according to claim 13 wherein the amount of the corrosion inhibiting compound(s) is 2 to 200 ppm.

15. A composition according to claim 4, wherein n is from 2 to 6.

* * * * *